United States Patent

Ogawa

(10) Patent No.: US 10,282,635 B2
(45) Date of Patent: May 7, 2019

(54) PATTERN INSPECTION APPARATUS

(71) Applicant: NuFlare Technology, Inc., Yokohama-shi (JP)

(72) Inventor: Riki Ogawa, Kawasaki (JP)

(73) Assignee: NuFlare Technology, Inc., Yokohama-shi (JP)

( * ) Notice: Subject to any disclaimer, the term of this patent is extended or adjusted under 35 U.S.C. 154(b) by 124 days.

(21) Appl. No.: 15/407,397

(22) Filed: Jan. 17, 2017

(65) Prior Publication Data

US 2017/0206433 A1    Jul. 20, 2017

(30) Foreign Application Priority Data

Jan. 18, 2016 (JP) ................................. 2016-007206

(51) Int. Cl.
  *G03F 1/84* (2012.01)
  *G06T 7/00* (2017.01)
  (Continued)

(52) U.S. Cl.
  CPC ............. *G06K 9/6203* (2013.01); *G03F 1/84* (2013.01); *G03F 7/702* (2013.01); *G06K 9/209* (2013.01);
  (Continued)

(58) Field of Classification Search
  CPC .............. G01N 21/88; G01N 21/8803; G01N 21/8806; G01N 21/95; G01N 21/956;
  (Continued)

(56) References Cited

U.S. PATENT DOCUMENTS 5,424,552 A * 6/1995 Tsuji .................... G03F 7/70241
  250/548
5,710,620 A * 1/1998 Taniguchi ........... G03F 7/70091
  355/53

(Continued)

FOREIGN PATENT DOCUMENTS

JP    2011-169743 A      9/2011
JP    2011169743 A   *  9/2011
(Continued)

OTHER PUBLICATIONS

Office Action dated Aug. 30, 2017 in Korean Patent Application No. 10-2017-0008561 (with English language translation).

*Primary Examiner* — Jamie J Atala
*Assistant Examiner* — Michael Robert Cammarata
(74) *Attorney, Agent, or Firm* — Oblon, McClelland, Maier & Neustadt L.L.P.

(57) ABSTRACT

According to one aspect of the present invention, a pattern inspection apparatus includes a first diaphragm that is positioned on an optical path of a reflection illumination optical system and has a first reference pattern of a line-and-space pattern formed thereon; a semi-transmission reflection plate configured to reflect a portion of a reference pattern image that has passed through the first reference pattern; a second diaphragm which is positioned on an optical path of the imaging optical system, on which the portion of the reference pattern image reflected by the semi-transmission reflection plate is projected, and which has a second reference pattern of a line-and-space pattern formed thereon; and a first time delay integration sensor (TDI sensor) configured to receive the portion of the reference pattern image that has passed through the second reference pattern.

10 Claims, 11 Drawing Sheets

(51) Int. Cl.
*H04N 5/372* (2011.01)
*G03F 7/20* (2006.01)
*G06K 9/20* (2006.01)
*G06K 9/62* (2006.01)
*G06T 7/73* (2017.01)
*H04N 5/225* (2006.01)
*H04N 5/235* (2006.01)
*G01N 21/956* (2006.01)
*H04N 5/374* (2011.01)

(52) U.S. Cl.
CPC ............. G06T 7/001 (2013.01); G06T 7/74 (2017.01); H04N 5/2256 (2013.01); H04N 5/2258 (2013.01); H04N 5/2351 (2013.01); *G01N 21/95607* (2013.01); *G01N 2021/95676* (2013.01); *G06T 2207/30148* (2013.01); *H04N 5/372* (2013.01); *H04N 5/3743* (2013.01)

(58) Field of Classification Search
CPC ... G01N 21/95607; G01N 2021/95676; G06K 9/6203; G06T 7/74; G06T 7/001; G06F 7/70483; G06F 7/70616; G06F 7/70625; G06F 7/7065
See application file for complete search history.

(56) References Cited

U.S. PATENT DOCUMENTS

| | | | |
|---|---|---|---|
| 6,151,122 A * | 11/2000 | Taniguchi | G03F 7/70358 356/399 |
| 6,879,381 B2 * | 4/2005 | Kenmoku | G03F 7/70258 355/52 |
| 9,417,533 B2 * | 8/2016 | Prosyentsov | G03F 1/44 |
| 2014/0104412 A1 * | 4/2014 | Inoue | G06T 7/00 |
| 2014/0111636 A1 * | 4/2014 | Inoue | G01N 21/956 348/92 |
| 2016/0011123 A1 * | 1/2016 | Shibata | G01N 21/956 356/237.5 |
| 2016/0370300 A1 * | 12/2016 | Ogawa | G01N 21/8851 |
| 2017/0108444 A1 * | 4/2017 | Otani | G01B 11/30 |
| 2018/0067057 A1 * | 3/2018 | Shmarev | G01N 21/8806 |

FOREIGN PATENT DOCUMENTS

| | | | |
|---|---|---|---|
| JP | 2011-257164 | | 12/2011 |
| JP | 2011257164 A | * | 12/2011 |
| KR | 10-2015-0073927 A | | 7/2015 |

* cited by examiner

PATTERN INSPECTION APPARATUS

CROSS-REFERENCE TO RELATED APPLICATION

This application is based upon and claims the benefit of priority from prior Japanese Patent Application No. 2016-007206 filed on Jan. 18, 2016 in Japan, the entire contents of which are incorporated herein by reference.

BACKGROUND OF THE INVENTION

Field of the Invention

Embodiments described herein relate generally to a pattern inspection apparatus. Embodiments described herein relate, for example, to a pattern inspection technique for inspecting pattern defects in an object to be a target object used to manufacture a semiconductor, and to an inspection apparatus that inspects an exposure mask substrate used in manufacturing a semiconductor element and a liquid crystal display (LCD).

Related Art

In recent years, the circuit line width required for semiconductor elements is getting even smaller due to increasing integration level and increasing capacity of a large-scale integrated circuit (LSI). These semiconductor elements may be manufactured by forming a circuit by transforming a pattern on a wafer through exposure by a reduction projection exposure apparatus, which is a so-called stepper, using an original pattern having a circuit pattern formed thereon (also called a mask or a reticle, and collectively called a mask hereinafter). Therefore, in order to manufacture a mask for transferring such a fine circuit pattern to a wafer, a pattern forming apparatus using electron beam, which can forma fine circuit pattern, is used. By using this type of pattern forming apparatus, a pattern circuit may be directly formed on a wafer. Other than electron beam, development of a laser beam forming apparatus, which forms a pattern using laser beam, has been attempted.

For manufacturing LSI requiring high manufacturing cost, improvement of yield is essential. However, as represented by a gigabit class dynamic random access memory (DRAM), a pattern for an LSI is in the order of submicron to nanometer. One of main factors for degradation of yield may be pattern defects in a mask used in transferring an ultrafine pattern to a semiconductor wafer by exposure of a photolithography technique. In recent years, a size of pattern defects that have to be detected becomes very small as size of an LSI pattern formed in a semiconductor wafer becomes finer. Therefore, high precision of a pattern inspection apparatus that inspects defects in a transfer mask used to manufacture LSIs is demanded.

As an inspection technique, there is a known method of inspecting by comparing an optical image obtained by capturing an image of a pattern formed on a target object such as a lithography mask with a predetermined magnification using an expansion optical system with an optical image obtained by capturing an image of the same pattern in design data or on a target object. Examples of pattern inspection methods include "die to die inspection" and "die to database inspection". In "die to die inspection", pieces of optical image data obtained by capturing an image of the same pattern at different positions on the same mask are compared. In "die to database inspection", pattern forming data (design pattern data) is obtained by converting format of CAD data of a designed pattern to an apparatus input format to be input by a forming apparatus when the pattern is formed using the CAD data as a mask, the pattern forming data is input to an inspection apparatus, the inspection apparatus generates a design image (reference image) based on the pattern forming data, and the design image is compared with an optical image serving as measurement data obtained by capturing an image of the pattern. In the inspection method performed by such an inspection apparatus, a target object is placed on a stage, and the target object is scanned with a luminous flux to inspect the target object. The target object is irradiated with a luminous flux by a light source and an illumination optical system. Light that has been transmitted through the target object or reflected by the target object forms an image on a sensor through the optical system. The image captured by the sensor is transmitted to a comparator circuit as measurement data. The comparator circuit compares the measurement data with the reference data with an appropriate algorithm after alignment of the images, and determines that a pattern defect is present when the images do not match.

Generally, in order to acquire a high-resolution image, an imaging system of an inspection apparatus has become a magnifying system. Thus, lenses having long focal distance have to be combined, necessarily resulting in a long optical path. Therefore, the imaging system is susceptible to the influence of air fluctuation. Since air fluctuation corresponds to variation of refractive index distribution in an optical path, air fluctuation works as an effect of bending a ray of light. This results in displacement of a pattern image on an imaging sensor. This displacement causes an error when the pattern image is compared with a reference image, and thus is a factor for preventing highly accurate inspection. Therefore, it is desirable that such displacement be measured. In regards of this issue, it is suggested to provide a four-divided sensor or the like as a sensor for measuring displacement separately from a sensor for imaging a mask pattern, image a cross pattern for measurement by the four-divided sensor or the like, and calculate the displacement (refer to, for example, JP 2011-257164 A).

BRIEF SUMMARY OF THE INVENTION

According to one aspect of the present invention, a pattern inspection apparatus includes a reflection illumination optical system configured to illuminate a substrate having a pattern formed thereon with reflection illumination light;

a first diaphragm that is positioned on an optical path of the reflection illumination optical system and has a first reference pattern of a line-and-space pattern formed thereon, the first reference pattern being configured to be irradiated with a portion of the reflection illumination light;

a semi-transmission reflection plate configured to reflect a portion of a reference pattern image that has passed through the first reference pattern;

an imaging optical system configured to form a pattern image of the substrate;

a second diaphragm which is positioned on an optical path of the imaging optical system, on which the portion of the reference pattern image reflected by the semi-transmission reflection plate is projected, and which has a second reference pattern of a line-and-space pattern formed thereon; and a first time delay integration sensor (TDI sensor) configured to receive the portion of the reference pattern image that has passed through the second reference pattern.

DETAILED DESCRIPTION OF THE INVENTION

First Embodiment

Hereinafter, in a first embodiment, a pattern inspection apparatus capable of obtaining displacement due to influence of air fluctuation on an optical image for inspection is described.

Figure 1:
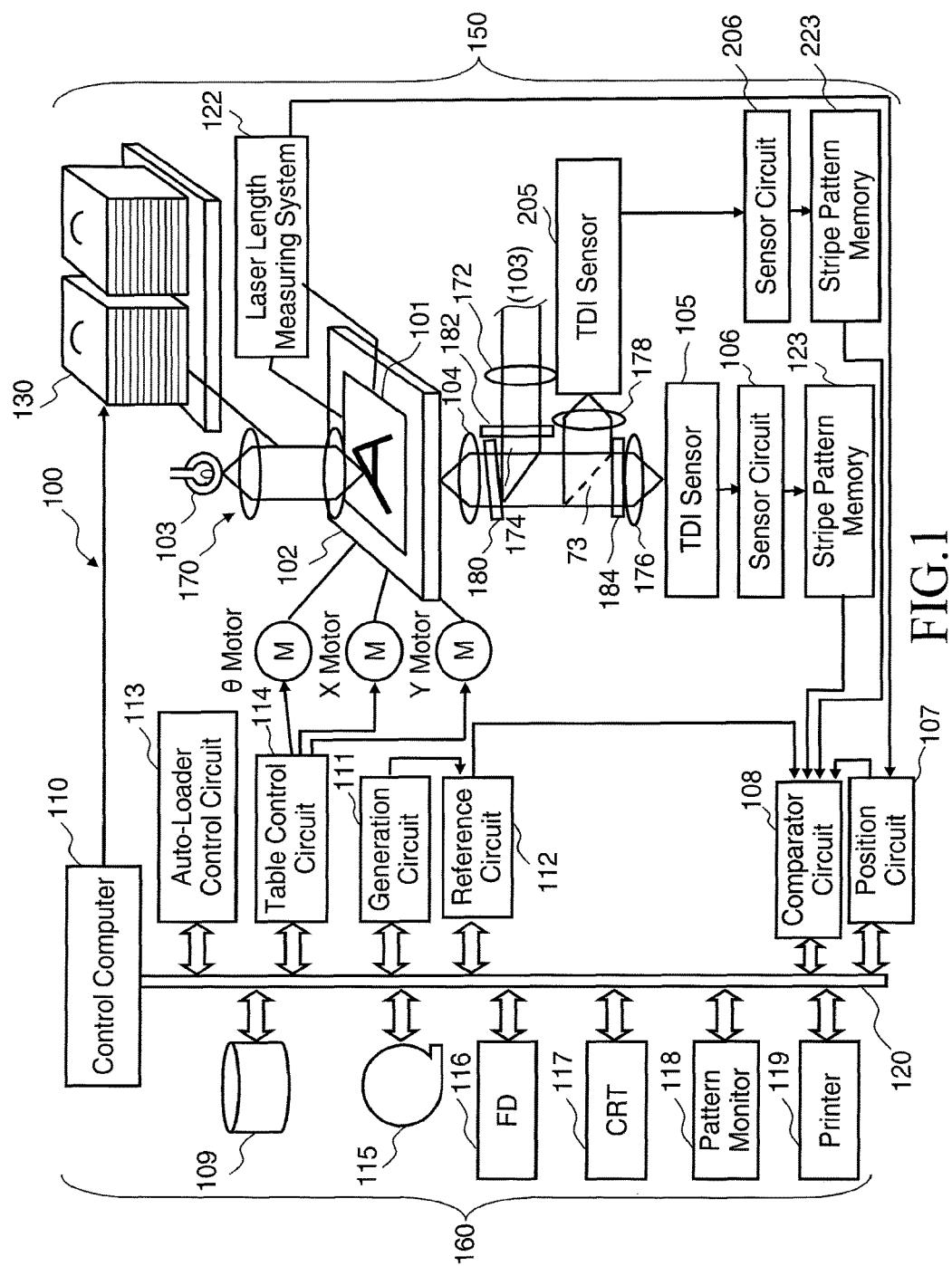
FIG. 1 is a configuration diagram illustrating a configuration of a pattern inspection apparatus according to a first embodiment.

FIG. 1 is a configuration diagram illustrating a pattern inspection apparatus according to the first embodiment. In FIG. 1, an inspection apparatus 100 that inspects defects in a pattern formed on a mask substrate 101 (an example inspection object substrate) includes an optical image acquisition unit 150 and a control system circuit 160 (controlling unit).

The optical image acquisition unit 150 includes a light source 103, a transmissive illumination optical system 170, an XYθ table 102 disposed movably, an objective lens 104, a semi-transmission reflection plate 180, a beam splitter 174, a reflection illumination optical system 172, an imaging optical system 176, a mirror 73, an imaging optical system 178, diaphragms 182 and 184, time delay integration (TDI) sensors 105 and 205 (example sensors), sensor circuits 106 and 206, stripe pattern memories 123 and 223, and a laser length measuring system 122. On the XYθ table 102, the mask substrate 101 (an example inspection object substrate) is placed. The mask substrate 101 may be, for example, an exposure photomask for transferring a pattern to a wafer. This photomask has a pattern formed thereon by a plurality of figures to be inspected. The mask substrate 101 may be positioned on the XYθ table 102 with its pattern formation surface facing downward.

The semi-transmission reflection plate 180 is a plate (film) that has both of reflection performance and transmission performance, and has character of reflecting a portion of light and transmitting a portion or whole of the rest of the light after the reflection. As the semi-transmission reflection plate 180, a quartz plate having one side non-coated can be used. Other than a quartz plate having one side non-coated, a plate that reflects a portion of light and transmits (a portion of) the rest of the light can be similarly used. In the first embodiment, a plate having reflectance of 5 to 15% may be preferably used. A plate having reflectance of 8 to 10% may be more preferably used. However, the semi-transmission reflection plate 180 is not limited to those plates, and a semi-transmission reflection plate having reflectance in a range of 1% to 99% inclusive (transmittance of 99% to 1% inclusive) may be used.

In the control system circuit 160, a control computer 110, which can be a computer, is connected via a bus 120 to a position circuit 107, a comparator circuit 108, a generation circuit 111, a reference circuit 112, an auto-loader control circuit 113, a table control circuit 114, a magnetic disk drive 109, a magnetic tape drive 115, a flexible disk device (FD) 116, a CRT 117, a pattern monitor 118, and a printer 119. In addition, the sensor circuit 106 is connected to the stripe pattern memory 123, and the stripe pattern memory 123 is connected to the comparator circuit 108. The sensor circuit 206 is connected to the stripe pattern memory 223, and the stripe pattern memory 223 is connected to the comparator circuit 108. The XYθ table 102 is driven by an X-axis motor, a Y-axis motor, and a θ-axis motor. The reflection illumination optical system 172 includes the objective lens 104 and the beam splitter 174.

In the inspection apparatus 100, a high-magnification inspection optical system includes the light source 103, the transmissive illumination optical system 170, the XYθ table 102, the objective lens 104 disposed movably, the semi-transmission reflection plate 180, the beam splitter 174, the reflection illumination optical system 172, the mirror 73, the imaging optical system 176, the imaging optical system 178, the diaphragms 182 and 184, the TDI sensors 105 and 205 (example sensors), and the sensor circuits 106 and 206. For example, an inspection optical system having magnification of 200 to 300 times is constituted.

The XYθ table 102 is driven by the table control circuit 114 under control of the control computer 110. The XYθ table 102 is movable by a driving system such as a three-axis (X-Y-θ) motor that drives in X direction, Y direction, and θ direction. As these X motor, Y motor, and θ motor, a linear motor, for example, may be used. The XYθ table 102 is movable in the horizontal direction and a rotation direction by respective motors of X, Y, and θ axes. A focal position (optical axis direction: Z-axis direction) of the objective lens 104 is dynamically adjusted to the pattern formation surface of the mask substrate 101 by an auto focusing control circuit that is not illustrated under control of the control computer 110. For example, the objective lens 104 is moved in the optical axis direction (Z-axis direction) by a piezoelectric element that is not illustrated, thereby adjusting a focal position of the objective lens 104. A moving position of the mask substrate 101 positioned on the XYθ table 102 is measured by the laser length measuring system 122 and supplied to the position circuit 107.

Design pattern data (pattern forming data) serving as a base of pattern formation of the mask substrate 101 is input from the outside of the inspection apparatus 100 and stored in the magnetic disk drive 109.

Note that FIG. 1 illustrates components necessary in describing the first embodiment. It goes without saying that the inspection apparatus 100 may include other components that are typically required.

Figure 2:
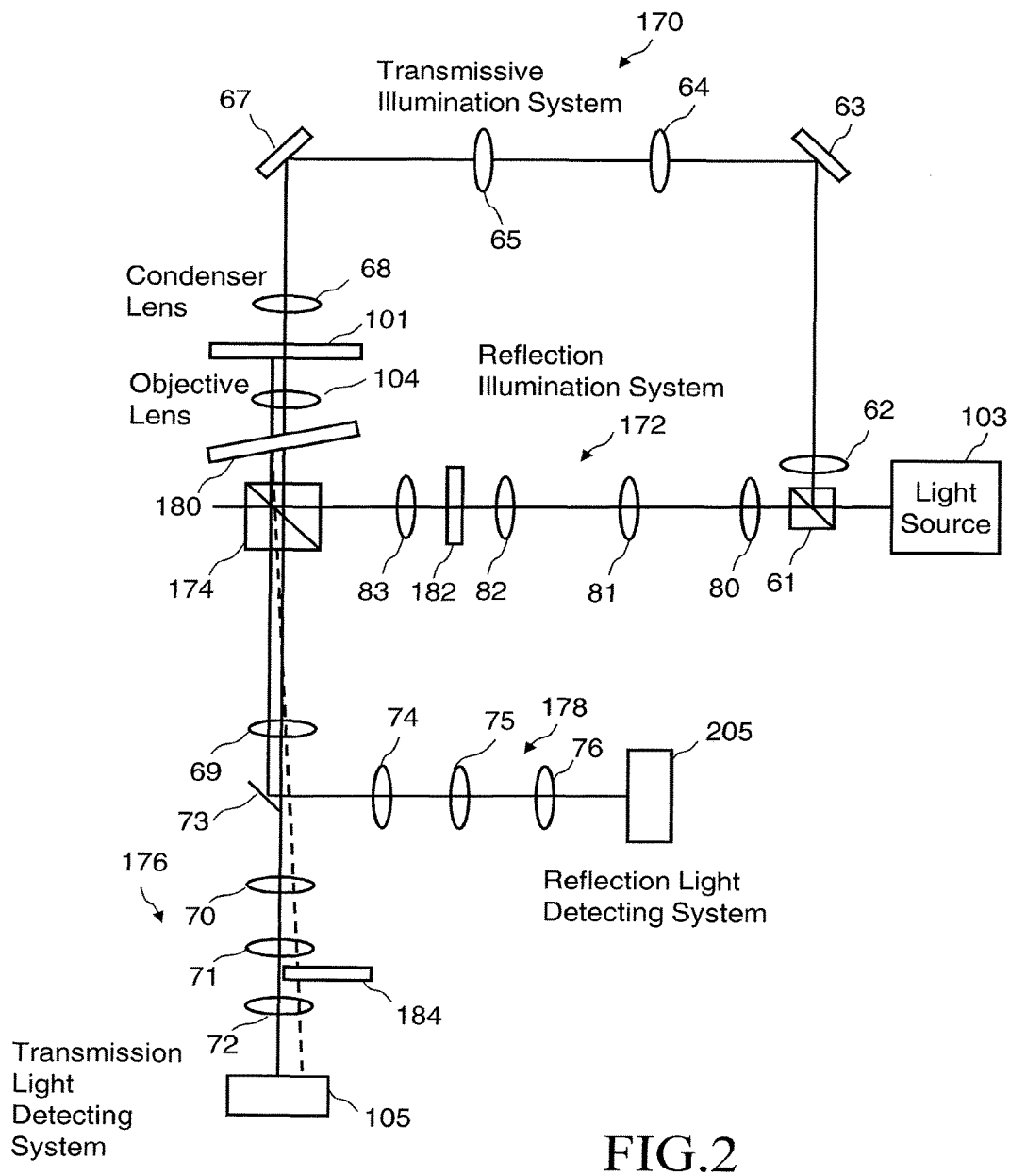
FIG. 2 is a view illustrating an example of a configuration of an optical system of an inspection apparatus according to the first embodiment.

FIG. 2 is a view illustrating an example of a configuration of the optical system of the inspection apparatus according to the first embodiment. In FIG. 2, from the light source 103, laser light having a wavelength equal to or shorter than the ultraviolet range (for example, deep ultraviolet (DUV) light) to be inspection light is generated. A portion of the generated light is reflected as light for illumination for transmission inspection by a beam splitter 61. Meanwhile, the rest of the generated light passes through the beam splitter 61 as light for illumination for reflection inspection.

The mask substrate 101 is illuminated with the light for illumination for transmission inspection (first inspection light) by the transmissive illumination optical system 170. A specific example is hereinafter described based on the example of FIG. 2. In the transmissive illumination optical system 170, light for illumination for transmission inspection obtained by splitting at the beam splitter 61 passes through a lens 62, is reflected by a mirror 63, passes through lenses 64 and 65, and is reflected by a mirror 67. The light that has been reflected by the mirror 67 forms an image on the pattern formation surface of the mask substrate 101 from the rear side, which is opposite to the pattern formation surface of the mask substrate 101, by means of a condenser lens 68. Transmission light, which has transmitted through the mask substrate 101, passes through the objective lens 104, the semi-transmission reflection plate 180, and the beam splitter 174. When the transmission light passes through the semi-transmission reflection plate 180, a portion of the transmission light is reflected and the rest thereof passes therethrough. The light that has passed through the beam splitter 174 passes through a lens 69 and enters the imaging optical system 176. The light then forms an image on the TDI sensor 105 (an example sensor) by means of the imaging optical system 176, and enters the TDI sensor 105 as an optical image. The light that has entered the imaging optical system 176 passes through a lens 70, passes through the diaphragm 184 (second diaphragm), and forms an image on the TDI sensor 105 by means of a lens 72 in the imaging optical system 176. The TDI sensor 105 (sensor) captures an optical image of a pattern formed on the mask substrate 101 while the XYθ table 102 with the mask substrate 101 placed thereon moves. Since light for transmission inspection needs not pass through the diaphragm 184, the diaphragm 184 may be arranged such that the light for transmission inspection passes through a position off the position of the diaphragm 184.

On the other hand, with light for illumination for reflection inspection (second inspection light), the mask substrate 101 is illuminated by the reflection illumination optical system 172. A specific example is hereinafter described based on the example of FIG. 2. In the reflection illumination optical system 172, light for illumination for reflection inspection that has passed through the beam splitter 61 passes through lenses 80, 81, and 82 and the diaphragm 182 (first diaphragm) is illuminated with the light for illumination for reflection inspection. The light that has passed through the diaphragm 182 is reflected by the beam splitter 174. A portion of the light that has been reflected by the beam splitter 174 is reflected by the semi-transmission reflection plate 180 and the rest of the light passes therethrough. The light that has passed through the semi-transmission reflection plate 180 enters the objective lens 104 and forms an image on the pattern formation surface of the mask substrate 101 from the side of the pattern formation surface of the mask substrate 101 by means of the objective lens 104. At this time, the light for illumination for reflection inspection forms an image at a position on the pattern formation surface of the mask substrate 101, the position being different from the position at which the light for illumination for transmission inspection forms an image as will be described later. Reflection light, which has been reflected by the mask substrate 101, passes through the objective lens 104, the semi-transmission reflection plate 180, and the beam splitter 174. When the reflection light passes through the semi-transmission reflection plate 180, a portion of the reflection light is reflected and the rest of the reflection light passes therethrough. The light that has passed through the beam splitter 174 passes through the lens 69, and it is then reflected by the mirror 73. The light that has been reflected by the mirror 73 enters the imaging optical system 178. The light then forms an image on the TDI sensor 205 (an example sensor) by means of the imaging optical system 178, and enters the TDI sensor 205 as an optical image. The light that has entered the imaging optical system 178 passes through lenses 74 and 75 and forms an image on the TDI sensor 205 by means of a lens 76 in the imaging optical system 178. The TDI sensor 205 (sensor) captures an optical image of a pattern formed in the mask substrate 101 (an example other pattern image of the substrate) while the XYθ table 102 with the mask substrate 101 placed thereon moves.

In this embodiment, the semi-transmission reflection plate 180 is arranged obliquely at an angle to the optical axis. Thus, out of the light for illumination for reflection inspection reflected by the beam splitter 174, the light reflected by the semi-transmission reflection plate 180 enters the beam splitter 174 at an angle different from the optical axis of the light for illumination for reflection inspection (different optical path) before the beam splitter 174, and passes through the beam splitter 174. The light that has passed through the beam splitter 174 passes through the lens 69 and enters the imaging optical system 176. The light then forms an image on the TDI sensor 105 (an example sensor) by means of the imaging optical system 176 and enters the TDI sensor 105 as an optical image. The light that has entered the imaging optical system 176 passes through the lens 70, passes through the diaphragm 184 (second diaphragm), and forms an image on the TDI sensor 105 by means of the lens 72 in the imaging optical system 176. When an image is formed on the TDI sensor 105, the image is formed in a region different from the region of the TDI sensor 105 where the light for illumination for transmission inspection forms an image as will be described later. That is, on the TDI sensor 105, light that has been reflected by the semi-transmission reflection plate 180 out of the light for illumination for transmission inspection and the light for illumination for reflection inspection forms an image. The diaphragm 184 is preferably positioned as close as possible to the final position of the imaging optical system 176 (close to the TDI sensor 105).

In the first embodiment, the transmissive illumination optical system 170 is configured such that light that has been reflected by the semi-transmission reflection plate 180 out of the light for illumination for reflection inspection forms an image on the TDI sensor 105 for transmission inspection, but other configuration is possible. The transmissive illumination optical system 170 may be configured such that light that has been reflected by the semi-transmission reflection plate 180 out of the light for illumination for reflection inspection forms an image on the TDI sensor 205 for reflection inspection. However, even in that case, the image is formed in a region different from the region of the TDI sensor 205 where the light for illumination for reflection inspection used for reflection inspection forms an image. That is, in that case, light that has passed through the semi-transmission reflection plate 180 out of the light for illumination for reflection inspection and light that has been reflected by the semi-transmission reflection plate 180 out of the light for illumination for reflection inspection form images in different regions (on different groups of photo detectors) in the light-receivable region of the TDI sensor 205.

The inspection apparatus 100 can perform one or both of inspection using transmission light and inspection using reflection light as described above. In order to perform only inspection using transmission light, it is enough to use information of the TDI sensor 105 for transmission inspection without using information of the TDI sensor 205 for reflection inspection. In order to perform only inspection using reflection light, it is enough to use information of the TDI sensor 205 for transmission inspection without using information of the TDI sensor 105 for reflection inspection. However, even in those cases, information of the TDI sensor 105 regarding light that has been reflected by the semi-transmission reflection plate 180 is used.

Figure 3A:
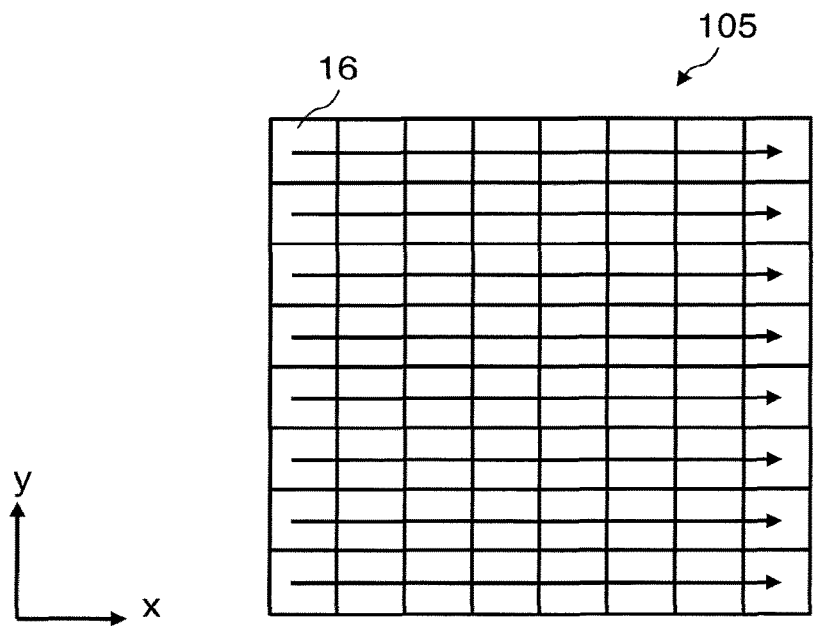
FIGS. 3A to 3E are views illustrating an example of an image-capturing method by a TDI sensor according to the first embodiment and examples of an image obtained by the image-capturing method.

FIGS. 3A to 3E are views illustrating an example of an image-capturing method by the TDI sensor according to the first embodiment and examples of an image obtained by the image-capturing method. In the TDI sensor 105 (205), a plurality of photo detectors 16 (photodiodes) that performs photoelectric conversion is arranged two-dimensionally, in other words, in an array as illustrated in FIG. 3A. Electric charge obtained through photoelectric conversion of each of the photo detectors 16 corresponding to amount of light received by the photo detector is sequentially transmitted to adjacent photo detector 16 in a direction opposite to an image-capturing direction (for example, x direction) at predetermined timing and stored. Thus, the XYθ table 102 is moved in a moving direction of electric charges in the TDI sensor 105 (a direction opposite to the image-capturing direction: for example, x direction) in synchronization with speed for transmitting electric charges in the TDI sensor 105 (205), so that electric charges at the same position on the mask substrate 101 obtained by different photo detectors 16 capturing an image are sequentially stored. Therefore, each position on the mask substrate 101 is respectively measured with electric charges that are total in an electric charge moving direction (for example, x direction) in the TDI sensor 105.

In the first embodiment, a reference pattern for measuring positional variation due to air fluctuation is formed in the diaphragm 182 separately from an opening for pattern inspection. The reference pattern image is then measured by the TDI sensor 105 using light that has been reflected by the semi-transmission reflection plate 180. The reference pattern formed in the diaphragm 182 does not move unlike the mask substrate 101 placed on the XYθ table 102. Therefore, electric charges stored by respective rows of the photo detectors 16 in the electric charge moving direction (for example, x direction) in the TDI sensor 105 are electric charges of the reference pattern at different positions.

Figures 3B, 3C:
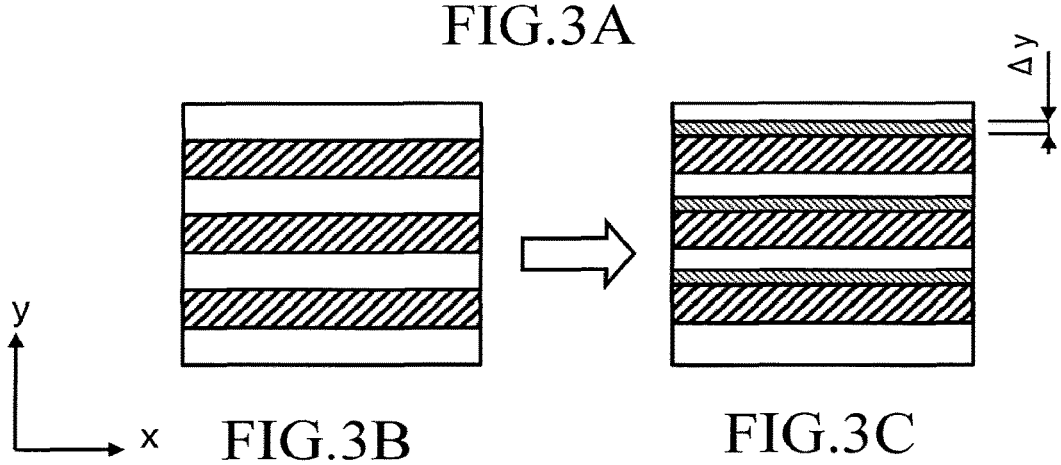

The reference pattern is assumed here to be a pattern of a shape that does not vary in the electric charge moving direction (for example, x direction) in the TDI sensor 105 as illustrated in FIG. 3B such as a line-and-space pattern including lines and spaces extending in x direction and arranged alternately in y direction. An image of the line-and-space pattern including lines and spaces extending in x direction and arranged alternately in y direction is captured by the TDI sensor 105. In that case, the rows of the photo detectors 16 arranged in x direction keep capturing images, for example, the same line patterns, and thus, a line-and-space pattern including lines and spaces extending in x direction and arranged alternately in y direction as illustrated in FIG. 3B is obtained. When air fluctuation occurs, the position of the pattern deviates in y direction by positional deviation (y-direction displacement: Δy) corresponding to the air fluctuation as illustrated in FIG. 3C. Thus, the positional deviation can be measured. For example, when the way of distortion varies in the same image, a region where deterioration by positional deviation in y direction (y-direction displacement Δy) corresponding to air fluctuation is generated, enabling measurement of the distortion.

Figures 3D, 3E:
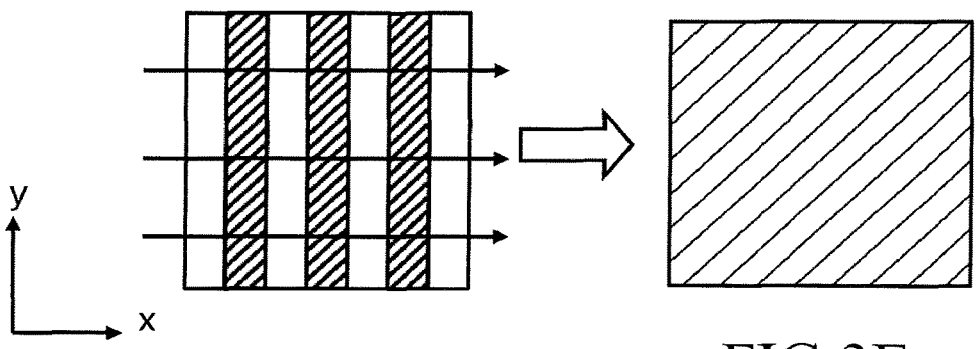

Meanwhile, the reference pattern is assumed to be a pattern of a shape that varies in the electric charge moving direction (for example, x direction) in the TDI sensor 105 as illustrated in FIG. 3D such as a line-and-space pattern including lines and spaces extending in y direction and arranged alternately in x direction. An image of the line-and-space pattern including lines and spaces extending in y direction and arranged alternately in x direction is captured by the TDI sensor 105. In that case, in each of the rows of the photo detectors 16 arranged in x direction, photo detectors 16 capturing an image of line pattern portions and photo detectors 16 capturing space pattern portions are mixed. Thus, whole of a pattern image obtained by cumulative addition becomes a gray pattern having gradation of 50% as illustrated in FIG. 3E. As a result, a line-and-space pattern cannot be identified. Therefore, even when air fluctuation occurs, it is difficult to measure positional deviation corresponding to the air fluctuation.

As described above, it is difficult for the TDI sensor 105 (205) to capture an image of a pattern of a shape that varies along the electric charge moving direction (for example, x direction) in the TDI sensor 105 while the pattern stops. Thus, it is difficult for the TDI sensor 105 (205) to measure displacement (for example, Δx) of the reference pattern image due to air fluctuation in the electric charge moving direction (for example x direction) in the TDI sensor 105. For this reason, it has been conventionally considered to provide a four-divided sensor or the like to measure displacement due to air fluctuation separately from the TDI sensor 105 (205). However, in the first embodiment, displacement due to air fluctuation in the electric charge moving direction (for example, x direction) in the TDI sensor 105 (205) is measured using the TDI sensor 105 (205), which is used to measure a pattern, by applying an approach as described below.

Figure 4A:
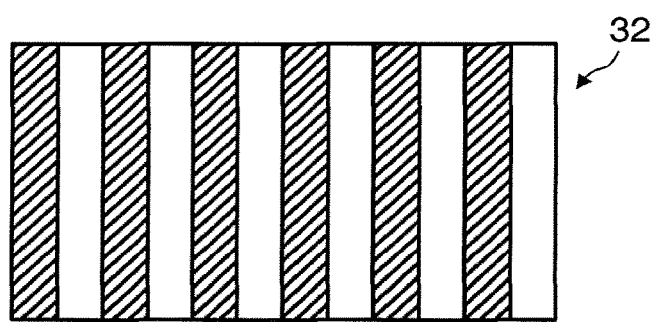
FIGS. 4A and 4B are views illustrating an example of combination of reference patterns according to the first embodiment.
Figure 4B:
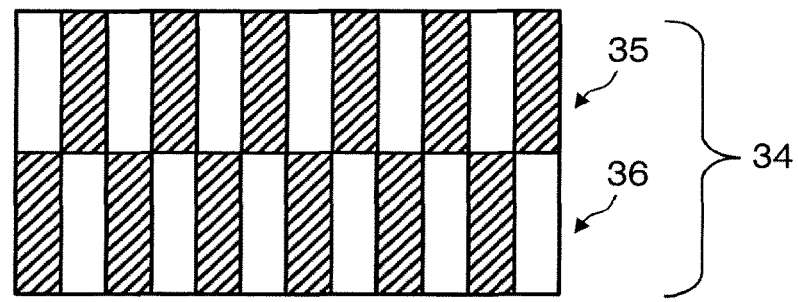

FIGS. 4A and 4B are views illustrating an example of combination of reference patterns according to the first embodiment. FIGS. 4A and 4B illustrate an example of a reference pattern for measuring displacement Δx in the electric charge moving direction (for example, x direction) in the TDI sensor 105 (205). On one of the diaphragms 182 and 184, a reference pattern 32 (first reference pattern) illustrated in FIG. 4A is formed, and on the other of the diaphragms 182 and 184, a reference pattern 34 (second reference pattern) illustrated in FIG. 4B is formed. In one of the reference patterns 32 and 34, two columns of line-and-space patterns are arranged such that opposite pattern type are connected, and in the other of the reference patterns 32 and 34, one column of line-and-space pattern is arranged. In the example illustrated in FIG. 4B, the reference pattern 34 is formed by arranging two columns of line-and-space pattern 35 and 36 (shaded portions indicate line patterns and blank portions indicate space patterns) such that opposite pattern types are connected. In the reference pattern 32, one column of line-and-space pattern (shaded portions indicate line patterns and blank portions indicate space patterns) is provided. The reference pattern 32 having one column of line-and-space pattern is formed to have height (height in y direction) equal to or more than total height of two columns of the line-and-space patterns 35 and 36 (height in y direction).

Figure 5A:
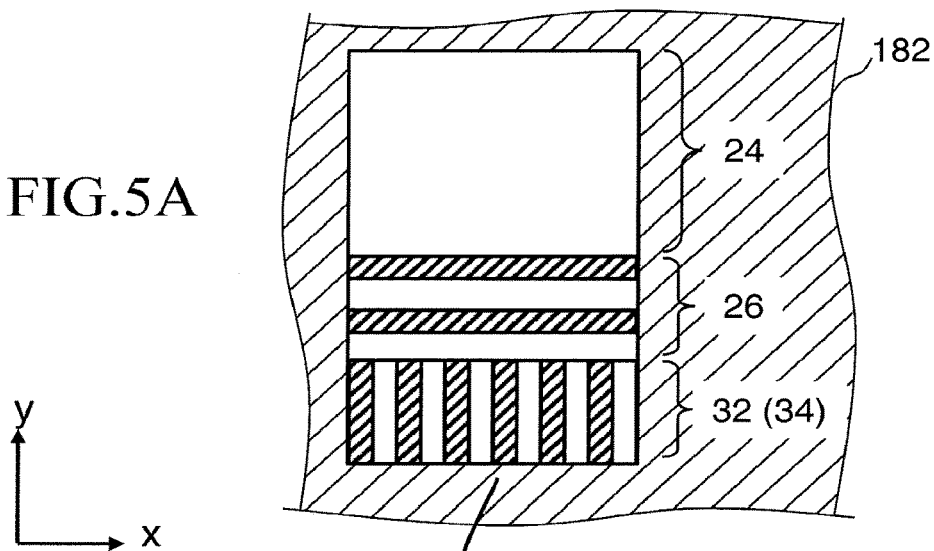
FIGS. 5A to 5C are views illustrating an example of a configuration of diaphragms and irradiation regions on a mask surface according to the first embodiment.
Figure 5B:
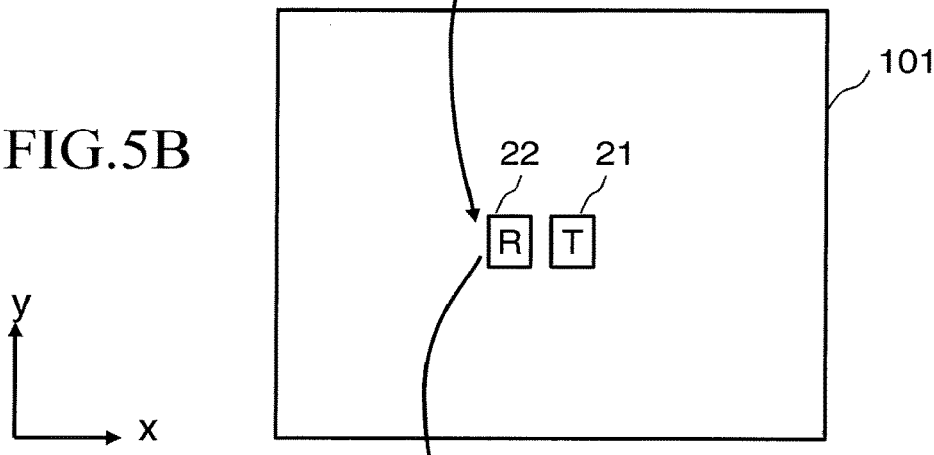
Figure 5C:
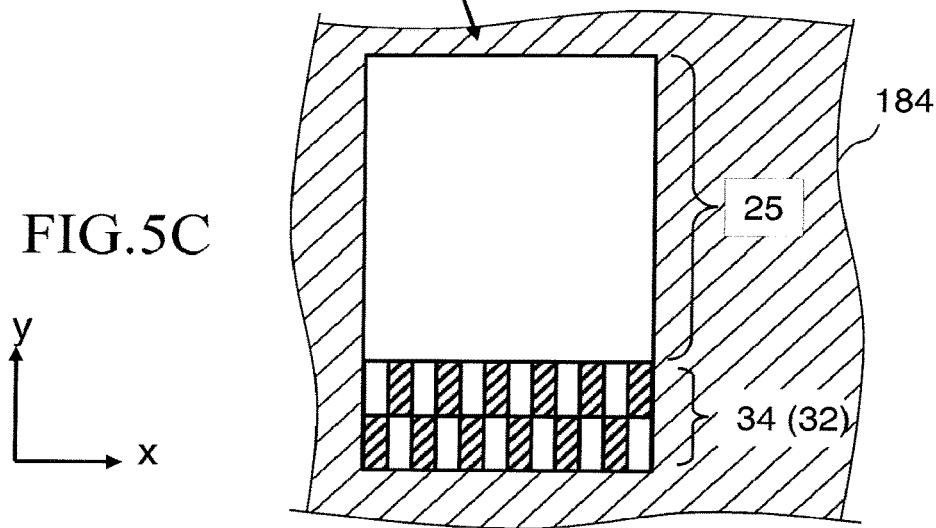

FIGS. 5A to 5C are views illustrating an example of a configuration of the diaphragms and irradiation regions on the mask surface according to the first embodiment. As illustrated in FIGS. 1 and 2, the diaphragm 182 (first diaphragm) is positioned on the optical path of the reflection illumination optical system 172. In the diaphragm 182, as illustrated in FIG. 5A, an opening 24 for reflection inspection, a reference pattern 26, and the reference pattern 32 (34) are formed. Through the opening 24, light for reflection inspection passes. The reference pattern 26 is for measuring displacement $\Delta y$ in a direction perpendicular to the electric charge moving direction of the TDI sensor 105 (205) (for example, y direction). The reference pattern 32 (34) is for measuring displacement $\Delta x$ in the electric charge moving direction of the TDI sensor 105 (205) (for example, x direction). Such a whole surface including the opening 24 for reflection inspection, the reference pattern 26, and the reference pattern 32 (34) is illuminated with the light for illumination for reflection inspection. In other words, the reference pattern 32 (34) is irradiated with a portion of the reflection illumination light. Regarding displacement $\Delta y$, an image of a pattern position can be captured as an image that can be identified by the TDI sensor 105 (205) as described referring to FIGS. 3B and 3C. Thus, it is enough when a line-and-space pattern including lines and spaces extending in x direction and arranged in y direction is formed as the reference pattern 26. Light (image) that has passed through the opening 24 for reflection inspection, the reference pattern 26, and the reference pattern 32 (34) is reflected by the beam splitter 174, passes through the semi-transmission reflection plate 180, and forms an image in a region 22 of the pattern formation surface of the mask substrate 101. Similarly, light for transmission inspection is irradiated on the pattern formation surface of the mask substrate 101, but forms an image on a region 21 as illustrated in FIG. 5B that is different from the region where the light for reflection inspection forms an image. Separating regions can prevent mixture of measuring patterns for transmission inspection and reflection inspection.

Meanwhile, out of light (image) that has passed through the opening 24 for reflection inspection, the reference pattern 26, and the reference pattern 32 (34), a portion that has been reflected by the semi-transmission reflection plate 180 enters the diaphragm (second diaphragm) positioned on the optical path of the imaging optical system 176. In the diaphragm 184, as illustrated in FIG. 5C, an opening 25 and the reference pattern (32) are formed. Through the opening 25, light for reflection inspection and an image of the reference pattern 26 for measuring displacement $\Delta y$ pass. On the reference pattern (32), the reference pattern 32 (34) for measuring displacement £x in the electric charge moving direction (for example, x direction) of the TDI sensor 105 (205) is projected.

Figure 6:
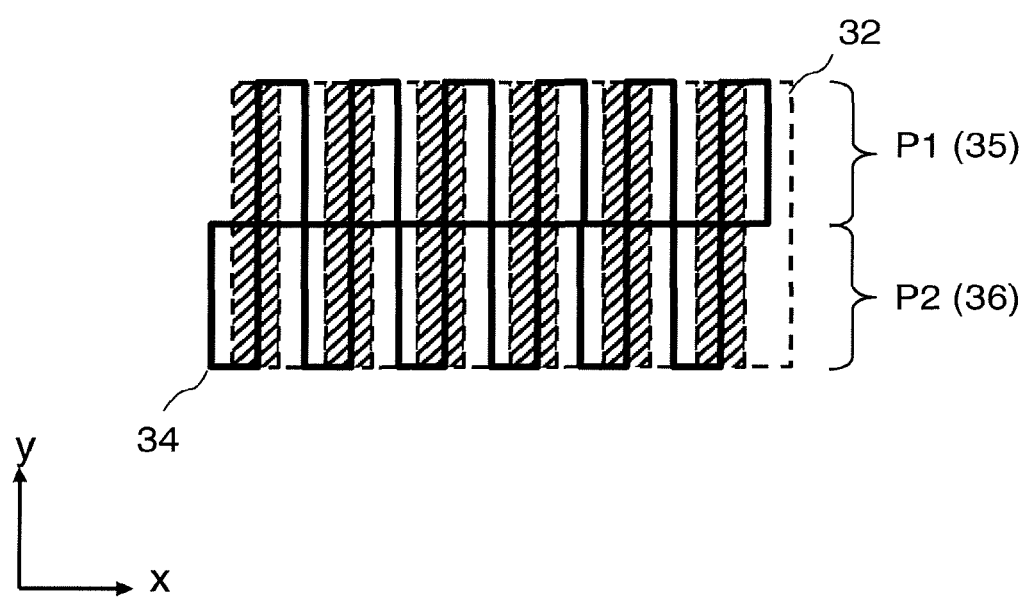
FIG. 6 is a view illustrating an example of an overlapping state of two reference patterns according to the first embodiment.

FIG. 6 is a view illustrating an example of an overlapping state of two reference patterns according to the first embodiment. An image of the reference pattern 32 (34) is projected on the reference pattern 34 (32) such that portions of line patterns overlap with each other, for example, positions of the line patterns deviate by half of the line patterns as illustrated in FIG. 6.

Figure 7:
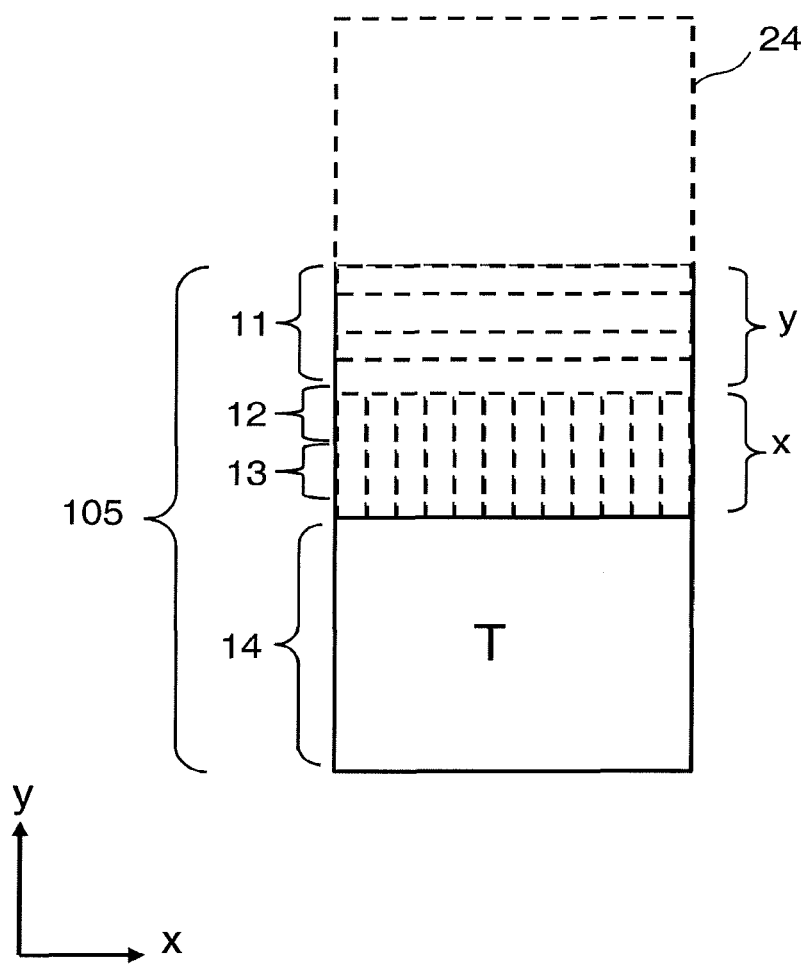
FIG. 7 is a view for describing positional relation of images on a light-receiving surface of a sensor for transmission inspection according to the first embodiment.

FIG. 7 is a view for describing positional relation of images on a light-receiving surface of a sensor for transmission inspection according to the first embodiment. As illustrated in FIG. 7, light for transmission inspection, and out of light (image) that has passed through the opening 24 for reflection inspection, the reference pattern 26, and the reference pattern (34), a portion that has been reflected by the semi-transmission reflection plate 180 enter the TDI sensor 105 for transmission inspection. At this time, incident positions of light for transmission inspection, and out of light (image) that has passed the opening 24 for reflection inspection, the reference pattern 26, and the reference pattern 32 (34), a portion that has been reflected by the semi-transmission reflection plate 180 are adjusted such that the lights are received by the photo detectors 16 in different regions. In an example of FIG. 7, light for transmission inspection enters a region 14 in the light-receiving surface where the plurality of photo detectors 16 of the TDI sensor 105 is arrayed. Light that has passed through the reference pattern 26 for measuring displacement $\Delta y$ enters a region 11. Light that has passed through the upper line-and-space pattern 35 (region P1) of the two columns of line-and-space pattern illustrated in FIG. 6 out of light for measuring displacement $\Delta x$ enters a region 12. Light that has passed through the lower line-and-space pattern 36 (region P2) of the two columns of line-and-space pattern illustrated in FIG. 6 out of light for measuring displacement $\Delta x$ enters a region 13. A region 24 off the light-receiving surface of the TDI sensor 105 is irradiated with light that has passed through the opening 24 for reflection inspection.

As described above, a plurality of photo detectors 16 arranged in the region 14 out of the plurality of photo detectors 16 of the TDI sensor 105 captures an image of a pattern for transmission inspection. A plurality of photo detectors 16 arranged in the region 11 captures an image of the reference pattern 26 for measuring displacement $\Delta y$. A plurality of photo detectors 16 arranged in the region 12 captures an image that has passed through the upper line-and-space pattern 35 (region P1). A plurality of photo detectors 16 arranged in the region 13 captures an image that has passed through the lower line-and-space pattern 36 (region P2).

Such positional relation can be accomplished by adjusting positions of the reference patterns 32 and 34 and an orientation angle of the semi-transmission reflection plate 180.

After the adjustment for receiving inspection light as described above, pattern inspection is started.

As an optical image-acquiring step (scan step), an optical image of the pattern formed on the mask substrate 101 is captured. At the same time, data (an image of the reference pattern 26 for measuring displacement $\Delta y$, an image that has passed through the upper line-and-space pattern 35 (region P1), and an image that has passed through the lower line-and-space pattern 36 (region P2)) for measuring displacement to calculate displacement due to air fluctuation is measured.

Figure 8:
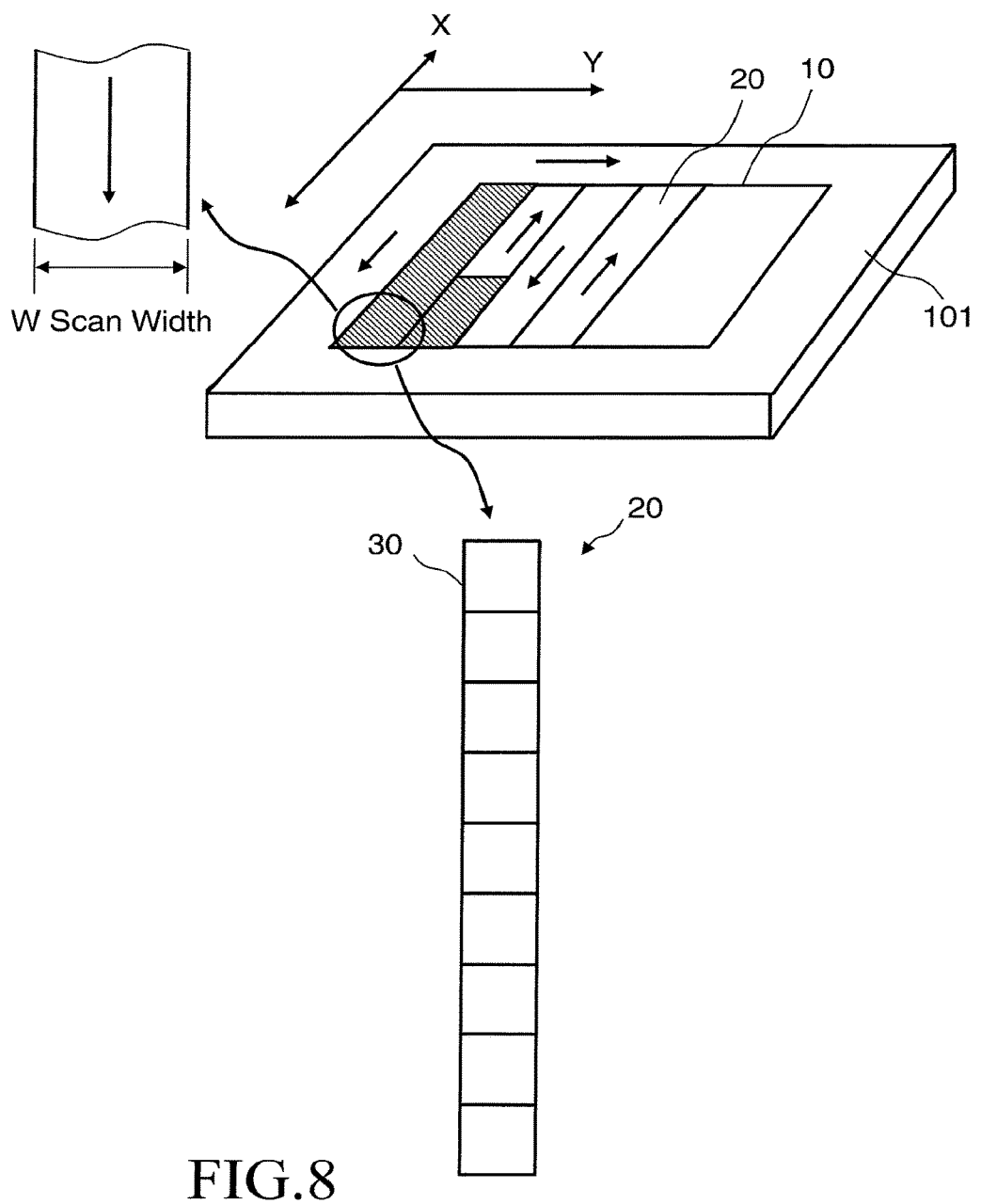
FIG. 8 is a schematic view for describing an inspection region according to the first embodiment.

FIG. 8 is a schematic view for describing an inspection region according to the first embodiment. An inspection region 10 (whole of the inspection region) of the mask substrate 101 is virtually divided, for example, into a plurality of inspection stripes 20 of a stripe shape having a scan width W in y direction as illustrated in FIG. 8. In the first embodiment, in addition to the pattern on the inspection stripes 20, an image of the reference pattern formed on the diaphragms 182 and 184 for displacement measurement is measured. Thus, a width that can be measured by photo detectors 16 other than photo detectors 16 in a region used for displacement measurement out of the plurality of photo detectors 16 of the TDI sensor 105 (205) is set to be the scan width W.

The inspection apparatus 100 then acquires images for the respective inspection stripes 20 (stripe region images). For the respective inspection stripes 20, images of figures positioned in the stripe regions are captured along a longitudinal direction (x direction) of the stripe regions using laser light. The XYθ table 102 is moved in x direction, resulting in acquisition of optical images while the TDI sensors 105 and 205 continuously move relative to each other in x direction. The TDI sensors 105 and 205 sequentially capture optical images of the scan width W as illustrated in FIG. 8. In other words, the TDI sensors 105 and 205, which are examples of a sensor, capture an optical image of the pattern formed on the mask substrate 101 using inspection light while moving relative to the XYθ table 102. In the first embodiment, after capturing of an optical image in one of the inspection stripes 20, the TDI sensors 105 and 205 move to a position of the next inspection stripe 20 in y direction and sequentially captures optical images of the scan width W similarly in the opposite direction this time. That is, image capturing is repeated in forward (FWD)-backward (BWD) directions, meaning that opposite directions in outward and homeward.

Here, the image-capturing direction is not limited to repeated forward (FWD)-backward (BWD). Image capturing may be performed in one direction. For example, FWD-FWD may be repeated. Alternatively, BWD-BWD may be repeated.

On an image of a pattern formed on the TDI sensor 105 for transmission inspection, photoelectric conversion is performed by the respective photo detectors 16 of the TDI sensor 105, and analog/digital (A/D) conversion is further performed by the sensor circuit 106. In the stripe pattern memory 123, pixel data of the inspection stripe 20 to be measured, and pixel data for measuring displacement when an image of the inspection stripe 20 to be measured is captured are stored. When such pixel data (stripe region images) is captured, as a dynamic range of the TDI sensor 105, for example, a dynamic range in which the maximum gradation is set to the condition where 60% of quantity of light of illumination light enters is used. When an optical image of one of the inspection stripes 20 is acquired, the laser length measuring system 122 measures a length to obtain a position of the XYθ table 102. The position information obtained by the length measurement is output to the position circuit 107. The position circuit 107 (calculating unit) calculates a position of the mask substrate 101 using the position information obtained by the length measurement.

Similarly, on an image of a pattern formed on the TDI sensor 205 for reflection inspection, photoelectric conversion is performed by the respective photo detectors 16 of the TDI sensor 205, and analog-digital (A/D) conversion is further performed by the sensor circuit 206. In the stripe pattern memory 223, pixel data of the inspection stripe 20 to be measured is stored. When such pixel data (stripe region images) is captured, as dynamic range of the TDI sensor 205, for example, a dynamic range in which the maximum gradation is set to the condition where 60% of quantity of light of illumination light enters is used. When an optical image of the inspection stripe 20 is acquired, the laser length measuring system 122 measures a length to obtain a position of the XYθ table 102. The position information obtained by the length measurement is output to the position circuit 107. The position circuit 107 (calculating unit) calculates a position of the mask substrate 101 using the position information obtained by the length measurement.

The respective stripe region images and the pixel data for measuring displacement when an image of the inspection stripe 20 to be measured is captured are then transmitted to the comparator circuit 108 along with data that indicates a position of the photomask 101 on the XYθ table 102 and that has been output from the position circuit 107. The measurement data (pixel data) may be, for example, 8-bit unsigned data and express gradation (quantity of light) of brightness of each pixel. The respective stripe region images output into the comparator circuit 108 and pixel data for measuring displacement when an image of the inspection stripes 20 to be measured are captured are stored in a storage device to be described later.

As a reference image creation step, first, the generation circuit 111 (an example reference image creation unit) performs image generation based on design pattern data as a base of forming a pattern for the mask substrate 101 to create a design image. Specifically, the generation circuit 111 reads design data from the magnetic disk drive 109 through the control computer 110, and converts each of the figures in regions of target frames 30 defined in the read design data to binary or multivalued image data (image generation) to create a design image.

In the present embodiment, the figure defined in the design pattern data is defined, for example, with a rectangle or a triangle as a basic figure. Figure data (vector data) that defines a shape, a size, a position, and the like of each pattern figure by information, for example, coordinates (x, y) at a reference position of the figure, length of sides, and a figure code as an identifier to distinct figure types such as a rectangle or a triangle is stored.

When information of a design pattern to be figure data is input to the generation circuit 111, the generation circuit 111 generates the information of data for each figure and interprets a figure code, a figure size, and the like indicating a figure shape of the figure data. The generation circuit 111 then generates binary or multivalued design image data as patterns to be positioned in unit squares each having a size of a grid of a predetermined quantization size and outputs the design image data. In other words, the generation circuit 111 reads design data, calculates occupancy rate of a figure in the design pattern for each of the squares obtained by virtually dividing the inspection region into unit squares each having a predetermined size, and outputs occupancy rate data of n bits. For example, one square may be preferably set to one pixel. When one pixel is made to have resolution of 1/28 (=1/256), the generation circuit 111 allocates small regions of 1/256 for regions of the figure positioned in the pixel, and calculates occupancy rate in the pixel. The generation circuit 111 then creates a design image of the occupancy rate data of 8 bits for each of the pixels. The design image data is output to the reference circuit 112.

The reference circuit 112 (an example reference image creation unit) performs filter processing on the design image to create a reference image.

Figure 9:
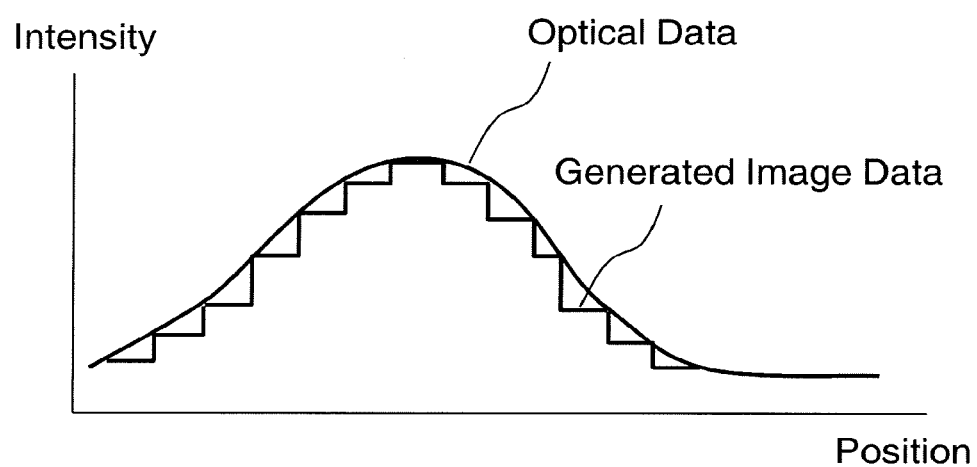
FIG. 9 is a view for describing filter processing according to the first embodiment.

FIG. 9 is a view for describing filter processing in the first embodiment. Measurement data as an optical image obtained from the sensor circuit 106 is in a state under effect of a filter due to resolution characteristics of the objective lens 104, an aperture plate effect of the TDI sensor 105, and the like, in other words in an analog state having continuous variation. Thus, reference design image data of design side image data having image intensity (grayscale value) of a digital value can match the measurement data by performing filter processing on the reference design image data. Thus, a reference image to be compared with a frame image (optical image) is created. The created reference image is output to the comparator circuit 108 and the reference image, which has been output into the comparator circuit 108, is stored in a storage device to be described later. As described above, image (reference image) data to be compared with for inspection is generated.

Figure 10:
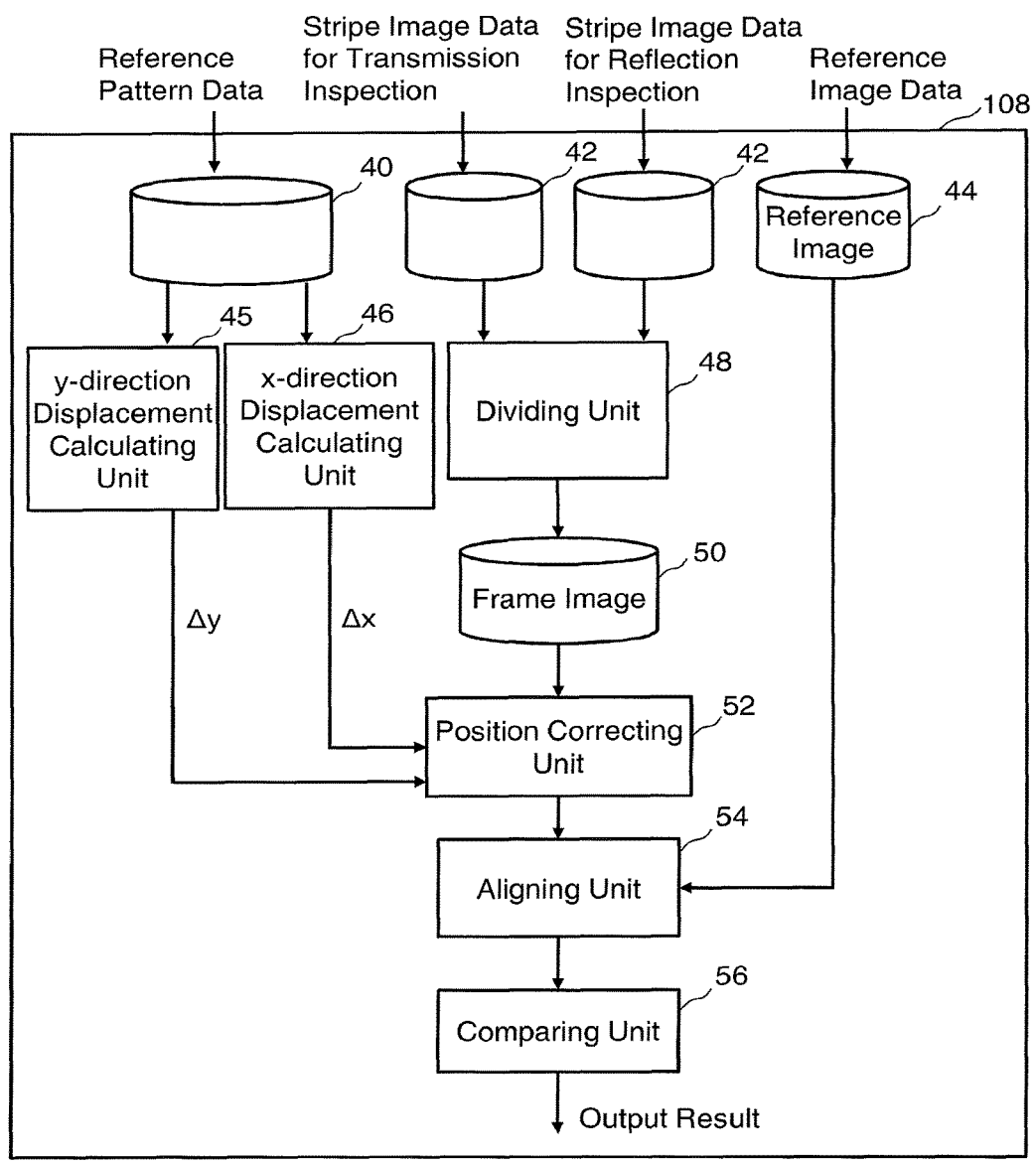
FIG. 10 is a view illustrating an internal configuration of a comparator circuit according to the first embodiment.

FIG. 10 is a view illustrating an internal configuration of a comparator circuit according to the first embodiment. In FIG. 10, in the comparator circuit 108, storage devices 40, 42, 44, and 50 such as magnetic disk drives, a y-direction displacement calculating unit 45, an x-direction displacement calculating unit 46, a frame dividing unit 48, a position correcting unit 52, an aligning unit 54, and a comparing unit 56 are disposed. Each of " . . . units" including the y-direction displacement calculating unit 45, the x-direction displacement calculating unit 46, the frame dividing unit 48, the position correcting unit 52, the aligning unit 54, and the comparing unit 56 has processing circuitry. Such processing circuitry includes, for example, an electric circuit, a computer, a processor, a circuit substrate, a quantum circuit, or a semiconductor device. Respective " . . . units" may use common processing circuitry (the same piece of processing circuitry), or different pieces of processing circuitry (separate pieces of processing circuitry). Information input to/output from the y-direction displacement calculating unit 45, the x-direction displacement calculating unit 46, the frame dividing unit 48, the position correcting unit 52, the aligning unit 54, and the comparing unit 56 and information under calculation is stored every time in a memory that is not illustrated.

A stripe region image for transmission inspection that has been output into the comparator circuit 108 is stored in the storage device 42. A stripe region image for reflection inspection output into the comparator circuit 108 is stored in the storage device 43. A reference image output into the comparator circuit 108 is stored in the storage device 44. Pixel data for measuring displacement when an image of the inspection stripe 20 to be measured is captured that has been output into the comparator circuit 108 is stored in the storage device 40.

As a step of calculating x-direction displacement of air fluctuation, the x-direction displacement calculating unit 46 (calculating unit) reads data for measuring x-direction displacement from the storage device 40, and multiplies light quantity variation of a reference pattern image that is received by the TDI sensor 105 (a portion of the image of a reference pattern that has been reflected by the semi-transmission reflection plate 180 out of the image of the reference pattern that has passed through the reference pattern 34) by a coefficient k to calculate the x-direction displacement of air fluctuation $\Delta x$. Specifically, the x-direction displacement calculating unit 46 (calculating unit) subtracts a quantity of light Q1 that has passed through the line-and-space pattern 35 (P1), which is one of the two columns of line-and-space pattern of the reference pattern 34, from a quantity of light Q2 that has passed through the line-and-space pattern 36 (P2), which is the other of the two columns, to obtain difference (Q2−Q1). The x-direction displacement calculating unit 46 adds the quantity of light Q1 that has passed through the line-and-space pattern 35 (P1), which is one of the two columns, to the quantity of light Q2 that has passed through the line-and-space pattern 36 (P2), which is the other of the two columns, to obtain a sum (Q1+Q2). The x-direction displacement calculating unit 46 then divides the difference (Q2−Q1) by the sum (Q1+Q2), and multiplies the resultant value by the coefficient k to calculate the x-direction displacement $\Delta x$. That is, the x-direction displacement $\Delta x$ can be defined by equation (1). The quantity of light Q1 can be defined as a total of quantity of light (gradation values) in an image captured by a plurality of photo detectors 16 positioned in the region 12 in the light-receiving surface of the TDI sensor 105. The quantity of light Q2 can be defined as a total of quantity of light (gradation values) in an image captured by a plurality of photo detectors 16 positioned in the region 13 in the light-receiving surface of the TDI sensor 105. The coefficient k may have been obtained through an experiment or the like.

$$\Delta x = k \cdot (Q2 - Q1)/(Q1 + Q2) \quad (1)$$

In FIG. 6, an image of the reference pattern 32 is projected in deviation from the reference pattern 34 by about a half of a line pattern (or a space pattern) to right (in +x direction). In this state, when the image of the reference pattern 32 is shifted to the right (in +x direction) due to, for example, air fluctuation, the quantity of light Q1 that has passed through the line-and-space pattern 35 (P1) is decreased. In contrast, the quantity of light Q2 that has passed through the line-and-space pattern 36 (P2) is increased. Meanwhile, when the image of the reference pattern 32 is shifted to the left (in −x direction) due to, for example, air fluctuation, the quantity of light Q1 that has passed through the line-and-space pattern 35 (P1) is increased. In contrast, the quantity of light Q2 that has passed through the line-and-space pattern 36 (P2) is decreased.

Air fluctuation varies over time. Therefore, during scan of the pattern formed on the mask substrate 101, when pixel data for displacement measurement is measured at the same time, light quantity variation in each period during the scan operation can be measured (calculated). It is difficult for a TDI sensor to capture an image of (image) a pattern varying in an electric charge moving direction such that the pattern is identifiable while the pattern stops. However, a TDI sensor can calculate a total of quantity of light in a preset region. Therefore, the TDI sensor 105 configured as in the first embodiment can measure the x-direction displacement $\Delta x$ in the electric charge moving direction of the TDI sensor 105.

Meanwhile, in the embodiment described above, a case where the reference pattern 32 of one column of line-and-space pattern is formed on the diaphragm 182 and the reference pattern 34 of the two columns of line-and-space pattern is formed on the diaphragm 184 has been described. On the contrary, when the reference pattern 34 of the two columns of line-and-space pattern is formed on the diaphragm 182 and the reference pattern 32 of one column of line-and-space pattern is formed on the diaphragm 184, (Q2−Q1) in equation (1) should be changed to (Q1−Q2). When the image of the reference pattern 34 is shifted to the right (in +x direction) due to, for example, air fluctuation, the quantity of light Q1 that has passed through the line-and-space pattern 35 (P1) is increased. In contrast, the quantity of light Q2 that has passed through the line-and-space pattern 36 (P2) is decreased. Meanwhile, when the image of the reference pattern 34 is shifted to the left (in −x direction) due to, for example, air fluctuation, the quantity of light Q1 that has passed through the line-and-space pattern 35 (P1) is decreased. In contrast, the quantity of light Q2 that has passed through the line-and-space pattern 36 (P2) is increased. The x-direction displacement $\Delta x$ is defined by equation (2).

$$\Delta x = k \cdot (Q1 - Q2)/(Q1 + Q2) \quad (2)$$

As described above, the x-direction displacement $\Delta x$ can be calculated.

As a step of calculating y-direction displacement of air fluctuation, the y-direction displacement calculating unit 45 reads data for measuring y-direction displacement from the storage device 40, creates an image of an image of a reference pattern (out of a reference pattern image that has passed through the reference pattern 26, a portion of the image of a reference pattern that has been reflected by the semi-transmission reflection plate 180) received by the TDI sensor 105, and calculates an amount of positional variation of the line pattern (or a space pattern) on the image as described with reference to FIG. 3C to calculate y-direction displacement $\Delta y$ of air fluctuation.

As a frame division step, the frame dividing unit 48 reads the stripe region images for transmission inspection from the storage device 42, and divides the stripe region images into pieces having a predetermined size in x direction (for example, a width as same as the scan width W) in such a manner that a frame image of a target frame region 30 is segmented from the stripe region images (optical images) of the inspection stripes 20. For example, the stripe region images are divided into frame images of 512×512 pixels. Similarly, the frame dividing unit 48 reads the stripe region images for reflection inspection from the storage device 43, and divides the stripe region images into pieces having a predetermined size in x direction (for example, a width that is the same as the scan width W) in such a manner that a frame image of a target frame region 30 is segmented from the stripe region images (optical images) of the inspection stripes 20. In other words, the stripe region images of the respective inspection stripes 20 are respectively divided into a plurality of frame images (optical images) having a width that is the same as the width of the inspection stripes 20, for example, the scan width W. Through such processing, a plurality of frame images (optical images) corresponding to the plurality of frame regions 30 is acquired. A plurality of frame images (optical images) for transmission inspection and a plurality of frame images (optical images) for reflection inspection are generated. The generated frame images (optical images) are stored in the storage device 50.

As a displacement correction step, the position correcting unit 52 (correcting unit) corrects relative positions of the frame image (pattern image) of the mask substrate 101 and the reference image using displacement ($\Delta x$, $\Delta y$) due to air fluctuation that has been calculated. In the example illustrated in FIG. 10, the position correcting unit 52 corrects a position of the frame image (pattern image) captured from the mask substrate 101.

Figures 11A, 11B:
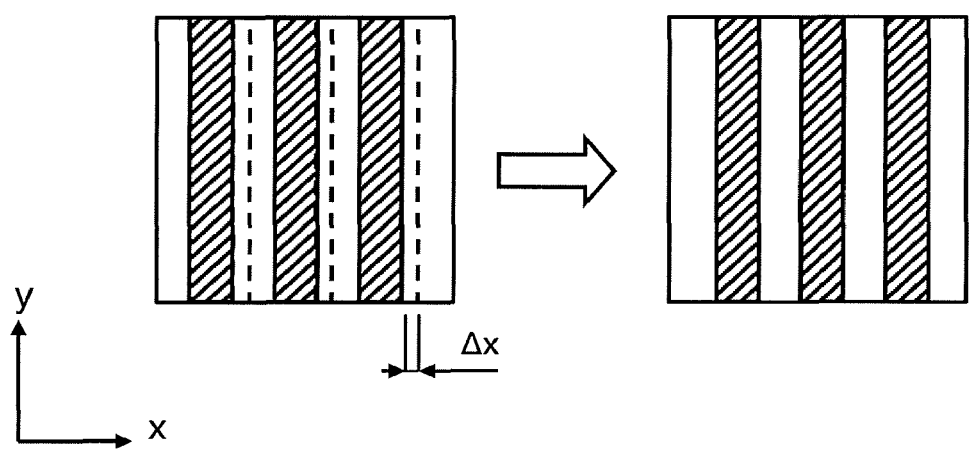
FIGS. 11A and 11B are views for describing displacement correction according to the first embodiment.

FIGS. 11A and 11B are views for describing displacement correction according to the first embodiment. As illustrated in FIG. 11A, when displacement $\Delta x$ due to air fluctuation is present in x direction, for example, the position of the pattern in the frame image is corrected such that the displacement $\Delta x$ is eliminated as illustrated in FIG. 11B. When displacement $\Delta y$ due to air fluctuation is present in y direction, a position of the pattern in the frame image is corrected such that the displacement $\Delta y$ is eliminated. Since air fluctuation varies over time, displacement ($\Delta x$, $\Delta y$) acquired at the same time as time of capturing an image is used to correct a position of the pattern in the frame image. The correction process is similar to a plurality of frame images (optical images) for transmission inspection and to a plurality of frame images (optical images) for reflection inspection.

As an alignment step, the aligning unit 54 aligns a frame image (optical image) to be compared and a reference image to be compared by a predetermined algorithm. For example, the images are aligned by least squares method.

As a comparison step, the comparing unit 56 compares a frame image (pattern image) of the substrate and a reference image in the corrected positional relation. Here, the comparing unit 56 compares those images for each pixel according to a predetermined determination condition, and determines presence/absence of a defect such as a shape defect. As a determination condition, for example, those images are compared for each pixel according to a predetermined algorithm to determine presence/absence of a defect. For example, the comparing unit 56 determines whether the difference between pixel values of those images is larger than a determination threshold, and determines that a defect is present when the difference is larger. The comparison result is then output. The comparison result may be output from the magnetic disk drive 109, the magnetic tape drive 115, the flexible disk device (FD) 116, the CRT 117, the pattern monitor 118, or the printer 119.

As described above, according to the first embodiment, displacement due to air fluctuation can be corrected prior to alignment of frame images (optical images) and reference images. An amount of deviation correction when images are aligned can be used as a positional deviation amount of the pattern itself formed on the mask substrate 101 from the design data. In other words, from a positional deviation amount of the pattern itself formed on the mask substrate 101 from the design data, displacement due to air fluctuation occurring in the inspection apparatus 100, especially in the imaging optical system, through which the pattern image of the mask substrate 101 passes can be eliminated.

As described above, according to the first embodiment, displacement of an optical image for inspection due to an influence of air fluctuation can be calculated. Therefore, highly accurate inspection is possible. In addition, when a TDI sensor captures a pattern image of the substrate, the need of providing a separate sensor for measuring displacement can be eliminated.

In the above description, "a . . . circuit" has processing circuitry. Such processing circuitry includes, for example, an electric circuit, a computer, a processor, a circuit substrate, a quantum circuit, or a semiconductor device. Respective " . . . units" may use common processing circuitry (the same piece of processing circuitry), or different pieces of processing circuitry (separate pieces of processing circuitry). When a program is used, the program may be recorded in a record carrier body such as a magnetic disk drive, a magnetic tape drive, an FD, or a read-only memory (ROM). For example, each circuit and the like in the position circuit 107, the comparator circuit 108, the generation circuit 111, the reference circuit 112, the auto-loader control circuit 113, and the table control circuit 114 has processing circuitry. Such processing circuitry includes, for example, an electric circuit, computer, a processor, a circuit substrate, a quantum circuit, or a semiconductor device.

An embodiment has been described with reference to the specific embodiment. However, the present invention is not limited to the specific embodiment.

Parts that are not needed directly for describing the present invention such as a device configuration and a control method have not been provided, but a device configuration and a control method that are needed can be appropriately selected and used. For example, a configuration of a controlling unit that controls the inspection apparatus 100 has not been described, but a controlling unit configuration that is needed can be appropriately selected and used, of course.

In addition, the scope of the present invention covers all pattern inspection apparatuses and all pattern inspection methods that each include elements of the present invention and that can be obtained by appropriate design change by a person skilled in the art.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern inspection apparatus comprising:
a reflection illumination optical system configured to illuminate a substrate having a pattern formed thereon with reflection illumination light;
a first diaphragm that is positioned on an optical path of the reflection illumination optical system and has a first reference pattern of a line-and-space pattern formed thereon, the first reference pattern being configured to be irradiated with a portion of the reflection illumination light;
a semi-transmission reflection plate configured to reflect a portion of a reference pattern image that has passed through the first reference pattern;
an imaging optical system configured to form a pattern image of the substrate;
a second diaphragm which is positioned on an optical path of the imaging optical system, on which the portion of the reference pattern image reflected by the semi-transmission reflection plate is projected, and which has a second reference pattern of a line-and-space pattern formed thereon; and
a first time delay integration sensor (TDI sensor) configured to receive the portion of the reference pattern image that has passed through the second reference pattern, wherein
the line-and-space pattern formed on the first diaphragm and the line-and-space pattern formed on the second diaphragm have line parts and space parts arranged alternately in a direction to which an electric charge moves in the first TDI sensor.

2. The apparatus according to claim 1 further comprising calculation processing circuitry configured to calculate displacement of air fluctuation by multiplying light quantity variation of the portion of the reference pattern image received by the first TDI sensor by a coefficient.

3. The apparatus according to claim 1, wherein
in one of the first and second reference patterns, two columns of line-and-space pattern are positioned such that opposite pattern types are connected, and in the other of the first and second reference patterns, one column of line-and-space pattern is positioned.

4. The apparatus according to claim 3, wherein
difference obtained by subtracting quantity of light that has passed through one line-and-space pattern of the two columns of line-and-space pattern from quantity of light that has passed through the other line-and-space pattern is divided by sum of the quantity of light that has passed through the one line-and-space pattern and the quantity of light that has passed through the other line-and-space pattern, and the resultant value is multiplied by the coefficient to calculate the displacement.

5. The apparatus according to claim 2, wherein
the first TDI sensor has a plurality of photo detectors arranged two-dimensionally, and
some photo detectors of the plurality of photo detectors receive light for calculating the displacement, and the others of the plurality of photo detectors images the pattern image of the substrate,
the apparatus further comprises:
correction processing circuitry configured to correct relative position between the pattern image of the substrate and a reference image by using the displacement calculated; and
comparison processing circuitry configured to compare the pattern image of the substrate and the reference image in the positional relation corrected.

6. The apparatus according to claim 1 further comprising a transmissive illumination optical system configured to illuminate the substrate with transmissive illumination light.

7. The apparatus according to claim 6, wherein
the portion of the reference pattern image that has passed through the second reference pattern is generated based on the reflection illumination light, and
the pattern image of the substrate is generated based on the transmissive illumination light.

8. The apparatus according to claim 7, wherein
the first TDI sensor receives the pattern image of the substrate that has been generated based on the transmissive illumination light and the portion of the reference pattern image that has passed through the second reference pattern and that has generated based on the reflection illumination light at the same time.

9. The apparatus according to claim 1, wherein
the pattern image of the substrate passes through a region of the second diaphragm, the region being different from a region through which the second reference pattern passes.

10. The apparatus according to claim 1 further comprising a second TDI sensor configured to receive another pattern image of the substrate generated based on another portion of the reflection illumination light that passes through a region of the first diaphragm, the region being different from a region through which the first reference pattern passes.

* * * * *